(12) United States Patent
Duval et al.

(10) Patent No.: US 10,661,070 B2
(45) Date of Patent: May 26, 2020

(54) BRACKET FOR FEEDING TUBE CONNECTOR

(71) Applicants: Ryan Nelson Duval, South Windsor, CT (US); Jill Susan Duval, South Windsor, CT (US)

(72) Inventors: Ryan Nelson Duval, South Windsor, CT (US); Jill Susan Duval, South Windsor, CT (US)

(73) Assignee: The TubieGuard LLC, South Windsor, CT (US)

( * ) Notice: Subject to any disclaimer, the term of this patent is extended or adjusted under 35 U.S.C. 154(b) by 29 days.

(21) Appl. No.: 15/264,155

(22) Filed: Sep. 13, 2016

(65) Prior Publication Data

US 2017/0071830 A1    Mar. 16, 2017

Related U.S. Application Data

(60) Provisional application No. 62/218,088, filed on Sep. 14, 2015.

(51) Int. Cl.
| | |
|---|---|
| *A61J 15/00* | (2006.01) |
| *A61M 39/10* | (2006.01) |
| *A61M 39/20* | (2006.01) |
| *A61M 39/08* | (2006.01) |
| *A61M 5/14* | (2006.01) |

(52) U.S. Cl.
CPC .......... *A61M 39/20* (2013.01); *A61M 5/1418* (2013.01); *A61M 39/08* (2013.01); *A61M 39/1011* (2013.01); *A61M 2039/087* (2013.01)

(58) Field of Classification Search
CPC ........ A61M 5/1417; A61M 2005/1588; A61M 2005/1586; A61M 2005/1416; A61M 2205/12; A61J 15/0053; A61J 15/0076; A61J 15/0026; A61B 50/20
See application file for complete search history.

(56) References Cited

U.S. PATENT DOCUMENTS

| | | | |
|---|---|---|---|
| 3,030,601 A | 4/1962 | Krebs | |
| 3,475,716 A | 10/1969 | Laig | |
| 3,881,753 A | 5/1975 | Bochory | |
| 4,183,603 A | 1/1980 | Donarummo | |
| 4,187,057 A * | 2/1980 | Xanthopoulos | ... A61M 5/14232 417/477.11 |
| 4,230,109 A | 10/1980 | Geiss | |
| 4,537,561 A * | 8/1985 | Xanthopoulos | ....... A61M 5/142 128/DIG. 12 |
| 4,641,646 A | 2/1987 | Schultz et al. | |

(Continued)

*Primary Examiner* — Nathan R Price
*Assistant Examiner* — Justin L Zamory
(74) *Attorney, Agent, or Firm* — Alix, Yale & Ristas, LLP

(57) ABSTRACT

A fluid delivery tube bracket is disclosed herein, comprising a central pocket formed by a rear wall, first and second end walls, and first and second side walls, the first end wall having a first slot configured to receive a first medical tube, and the second end wall having a second slot configured to receive a second medical tube. The first side wall includes a first port plug receiving portion configured to receive a first connector plug when in an open position, and the second side wall includes a second port plug receiving portion configured to support a second port plug when in a closed position. Additional product and method embodiments also are disclosed.

18 Claims, 11 Drawing Sheets

(56) References Cited

U.S. PATENT DOCUMENTS

| | | | | |
|---|---|---|---|---|
| 4,668,225 | A | * | 5/1987 | Russo ................ A61J 15/0015 604/104 |
| 4,723,947 | A | | 2/1988 | Clark et al. |
| 4,832,618 | A | | 5/1989 | Gunderson |
| 5,037,405 | A | | 8/1991 | Crosby |
| 5,057,093 | A | | 10/1991 | Clegg et al. |
| 5,772,409 | A | * | 6/1998 | Johnson ................ F04B 43/082 128/DIG. 12 |
| 6,267,754 | B1 | | 7/2001 | Peters |
| 7,887,515 | B2 | | 2/2011 | Bierman |
| 8,287,495 | B2 | * | 10/2012 | Michaud ............ A61M 5/1413 604/122 |
| 8,535,082 | B2 | | 9/2013 | Lifson |
| 8,585,655 | B2 | | 11/2013 | Bierman |
| 8,608,705 | B2 | | 12/2013 | Peters et al. |
| 2012/0197191 | A1 | | 8/2012 | DeLegge |
| 2013/0214655 | A1 | * | 8/2013 | Sharpe ...................... A61J 1/16 312/209 |
| 2015/0157845 | A1 | | 6/2015 | Bayly |
| 2015/0290449 | A1 | | 10/2015 | Yanik |

* cited by examiner

BRACKET FOR FEEDING TUBE CONNECTOR

BACKGROUND

Gastric feeding tubes, also known as enteral feeding tubes or enteric feeding tubes, are typically used to introduce nutritional substances or other prescribed products directly into the gut of a patient. The products are typically in a "soupy" form of liquid and solid or liquid only. The tubes have a distal end positioned in the patient's stomach or intestine, from which the nutritional substance is released. The distal (inside) end of the tube is held in place by a water filled balloon or the like.

The proximal (outer) end of the gastric feeding tube is typically connected to an enteral administration set which in turn is connected to a container having a prescribed product therein. The nutritional product may be delivered by gravity feed or more commonly by means of a pump. In either arrangement there is some pressure in the feeding tube and the connections that are necessary to join the container of nutritional product to the outside end of the gastric feeding tube. One of the problems associated with enteral feeding is the unintentional disconnection of the feeding supply tube from the connector on the outer end of the gastric feeding tube.

It is common for enteric feeding to take place overnight, while the patient is in bed. Patients, particularly children, are prone to moving during sleep in ways that can result in inadvertent disconnection of the feeding supply tube, which results in an alarm and significant disruption of patient rest. Further, it is common for the connector to include a Y-port for delivery of medication via the gastric feeding tube. Such a Y-port connector is shown in U.S. Pat. No. 5,322,073. The medication port has a plug to close the port when not in use, e.g., during feeding. Patient movement may kink the portion of the gastric tube between the Y-port connector and the patient's abdomen, which can cause pressure to accumulate and push the plug out of the medication port. This can result in nutritional product flowing out of the medication port until the issue is discovered.

Feeding pumps are equipped to sound an alarm when: 1) the feeding bag is not properly placed inside the door of the pump; 2) there is air in the line of the feeding bag; or 3) there is a kink in any of the tubes resulting in a "no flow" error message. However, the pump does not alarm if the feeding bag is disconnected from the feeding tube of the patient. For example, if the feeding tube is disconnected during a continuous night feed of 10 hours, which does not cause the pump to alarm, the result can be anywhere from 1-10 hours of the nutritional product released into the patient's bed. Not only is this a mess, but the patient is not receiving the prescribed nutrition.

Many conditions require a patient to need a feeding tube. Whether the patient is not allowed to eat by mouth at all or the patient needs supplemental calories in addition to what they eat by mouth, the fact remains that getting the calories successfully into the patient is vital for them to remain healthy. Losing these very important calories due to one of the aforementioned mishaps can cause major issues for these patients.

It is an object of the disclosure to provide a cost effective, simple product that will reduce problems associated with disconnection of feeding supply tubes and/or unintended opening of medication ports in enteric feeding apparatus.

SUMMARY

One embodiment described herein is a fluid delivery tube bracket, comprising a central pocket formed by a rear wall, first and second end walls, and first and second side walls. The first end wall has a first slot configured to receive a first medical tube. The second end wall has a second slot configured to receive a second medical tube. The first side wall includes a first port plug receiving portion configured to receive a first port plug when in an open position. The second side wall includes a second port plug receiving portion configured to support a second port plug when in a closed position. In embodiments, the first and second medical tubes are held in place in the first and second slots by an interference fit.

Another embodiment is a medical tube system comprising a Y-port connector having an outlet end connected to a fluid delivery tube, and an inlet end connected to a fluid supply tube. The Y-port connector includes a first port at the inlet end configured to receive a first plug, and a second port configured to receive a second plug. The feeding tube system further includes a medical fluid delivery tube bracket comprising a central pocket formed by a rear wall, first and second end walls, and first and second side walls. The first end wall has a first slot configured to receive the fluid supply tube. The second end wall has a second slot configured to receive the fluid delivery tube. The first side wall includes a first port plug receiving portion configured to receive a first port plug when in an open position, and the second side wall includes a second port plug receiving portion configured to support the second port plug when in a closed position.

A further embodiment is a bracket for a fluid delivery tube, the bracket comprising a central pocket formed by a rear wall, first and second end walls, and first and second side walls. The first end wall has a first slot configured to receive a first medical tube. The second end wall has a second slot configured to receive a second medical tube. The first side wall has a first port plug receiving portion formed therein configured to receive a port plug when in an open position. The bracket has at least one of a front wall comprising a viewing window and an open front to permit viewing inside the central pocket.

A further embodiment is a method of 3D printing the brackets described above.

In one embodiment, the disclosed bracket is configured to surround and protect the feeding tube Y-port connector so that it cannot be tampered with or be inadvertently disconnected. The disclosed bracket also prevents the plug or stopper for a medication port from being dislodged or opened unintentionally. In embodiments, the bracket is a one piece, substantially rigid part that defines a pocket configured to receive the Y-port connector and includes openings at opposite ends for the parts of the feeding tube connected by the Y-port. The pocket has a depth sufficient to receive the Y-port connector so that little or none of the Y-port connector protrudes above a lip of the pocket. This prevents the Y-port connector from being caught on clothing or bedding and reduces the likelihood of patient tampering.

DETAILED DESCRIPTION OF THE DISCLOSED EMBODIMENTS

Figure 1:
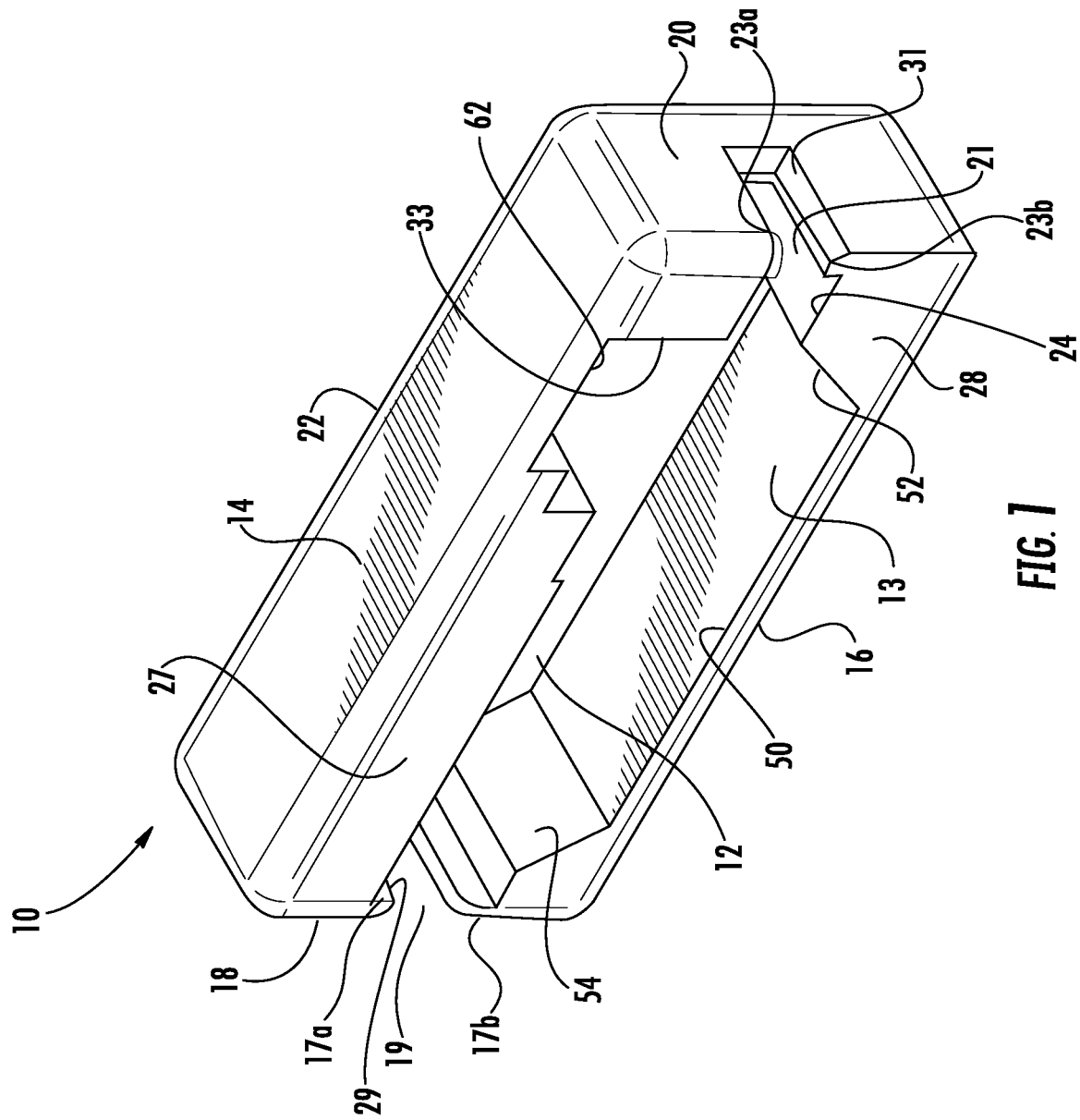
FIG. 1 is a perspective view of the disclosed bracket.
Figure 2:
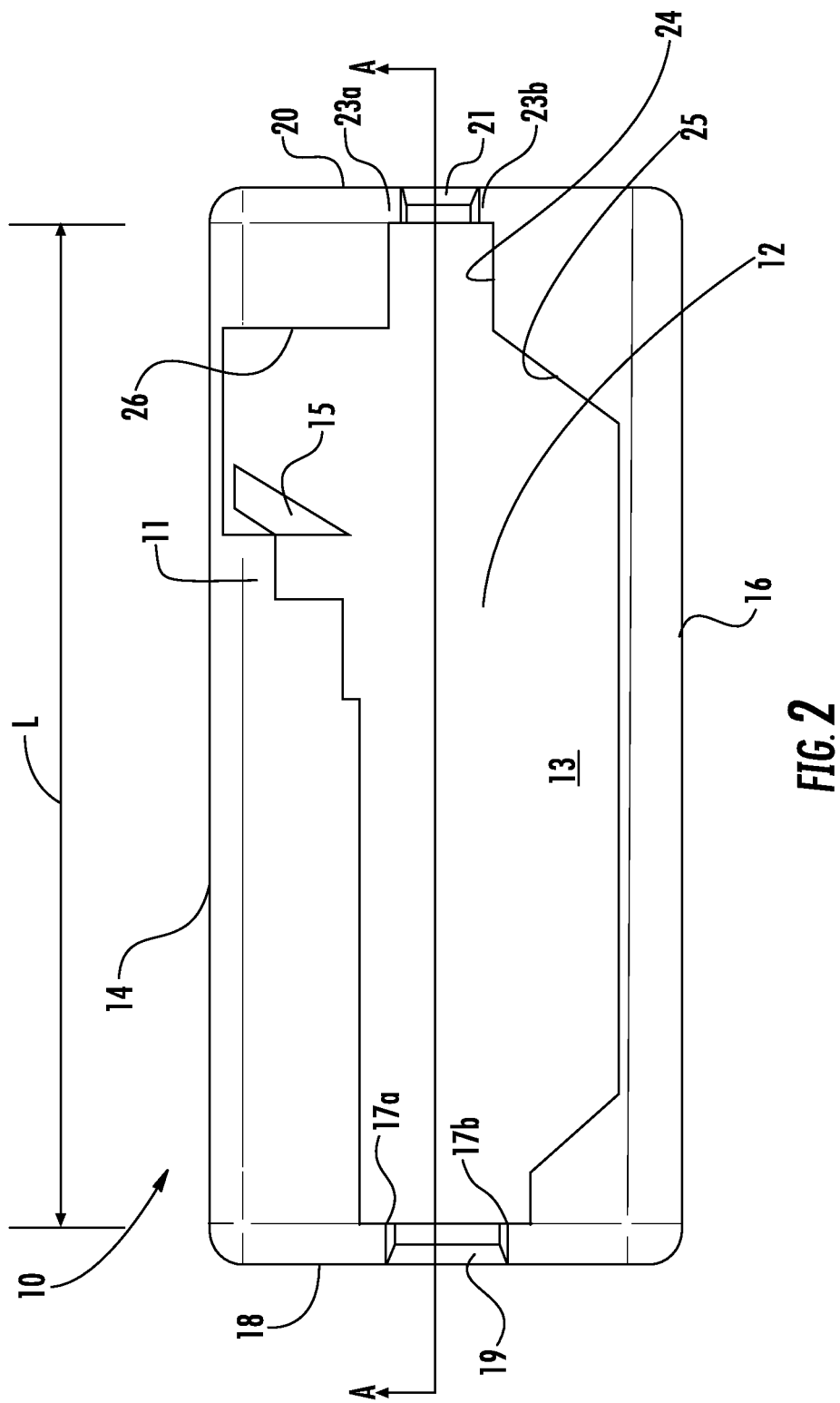
FIG. 2 is a top plan view of the bracket of FIG. 1.
Figure 3:
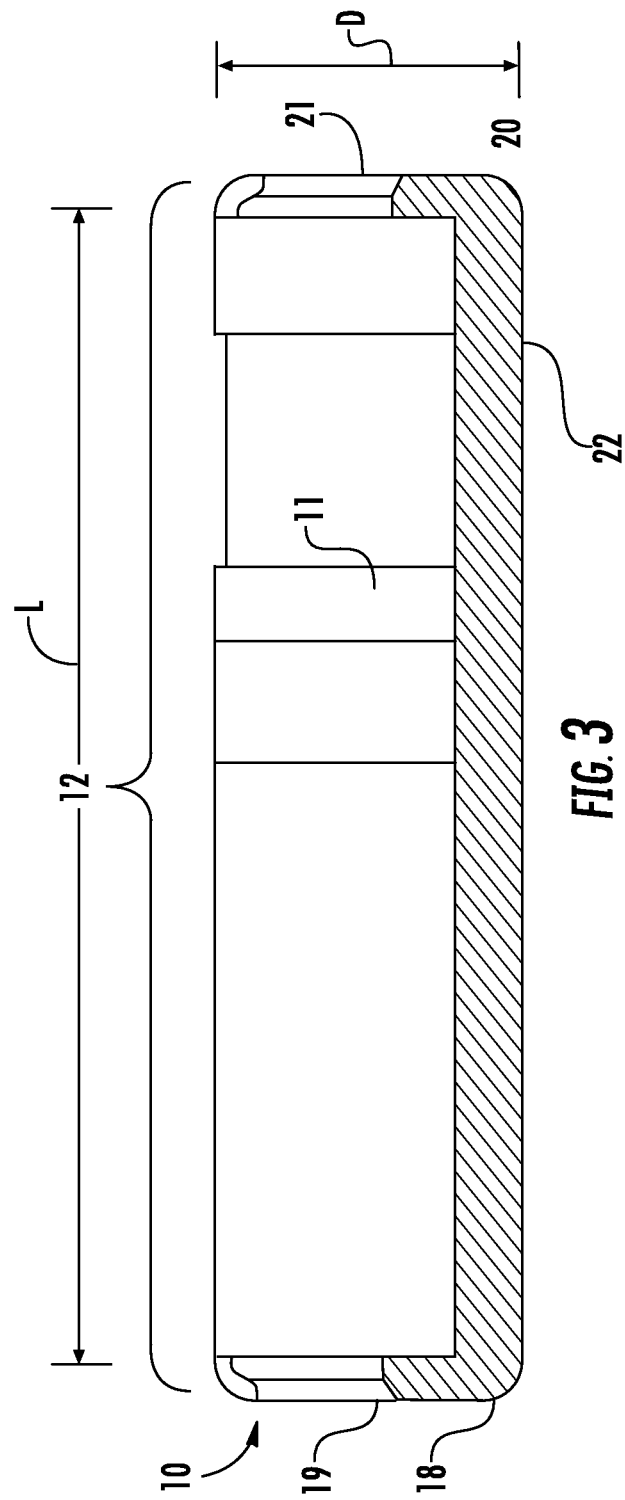
FIG. 3 is a longitudinal sectional view through the disclosed bracket, taken along line AA of FIG. 2.
Figure 4:
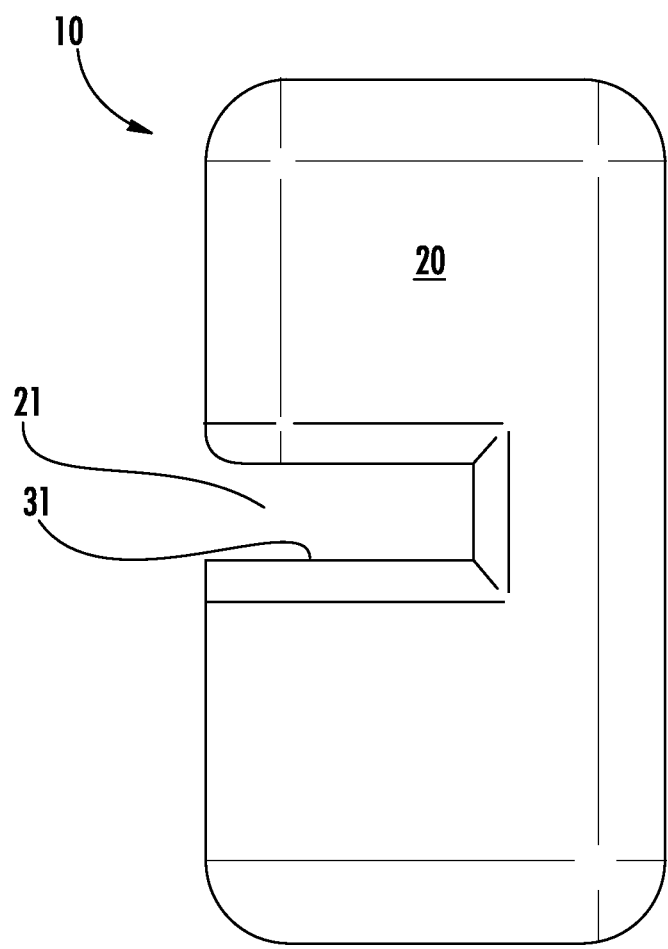
FIG. 4 is a right end view of the bracket of FIGS. 1-3.
Figure 5:
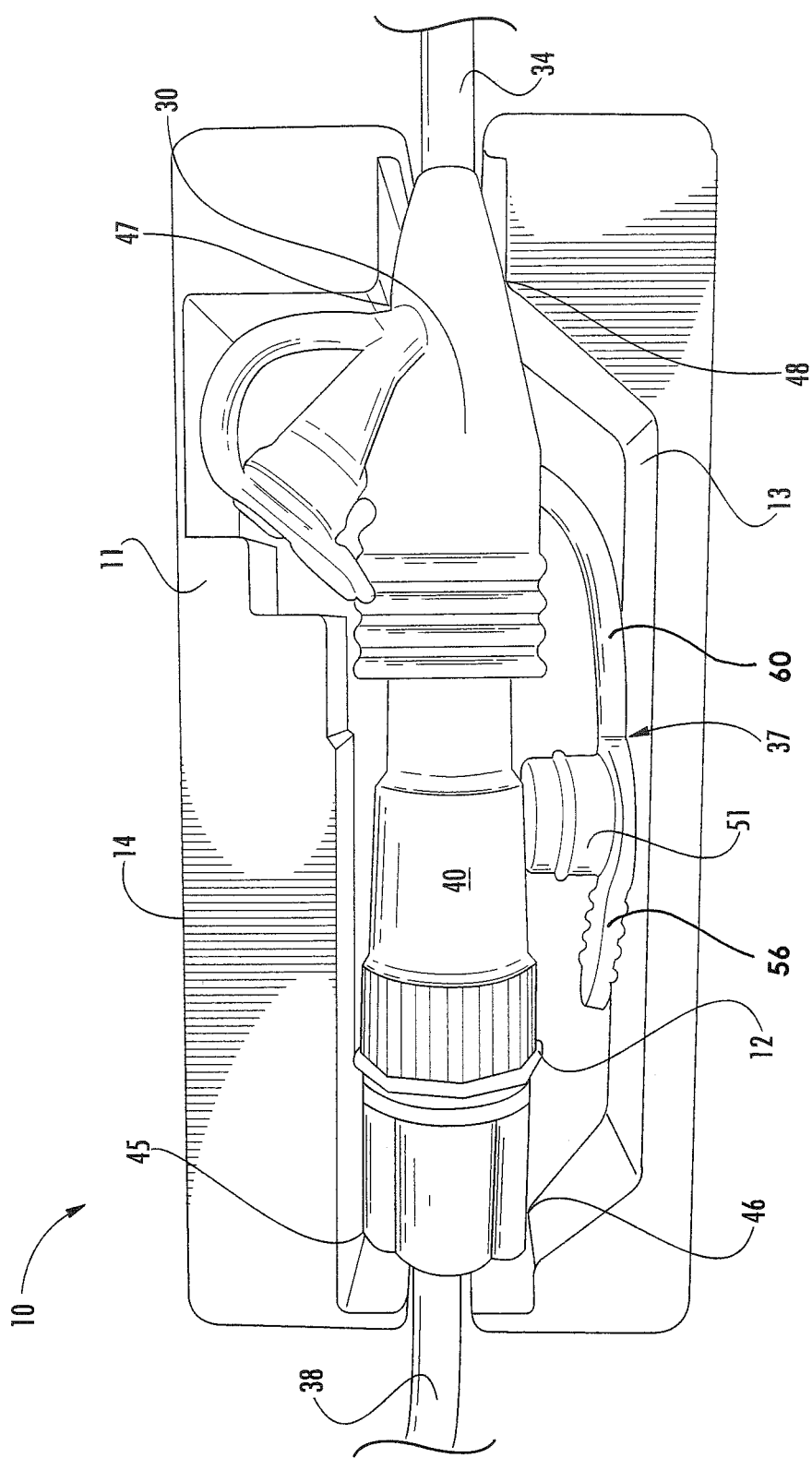
FIG. 5 shows the disclosed bracket with a received Y-port connector and associated feeding tubes.

FIGS. 1-5 illustrate one embodiment of the disclosed bracket, which will be referred to by the reference numeral 10. Those skilled in the art will recognize that the concept for the bracket is not limited to the disclosed embodiment and alternative structural arrangements, materials and manufacturing methods may be employed to provide the disclosed functionality. The disclosed embodiment of a bracket 10 is a single piece substantially rigid part that defines a multi-section pocket configured to receive and retain an assembly of a Y-port connector and associated feeding tubes as shown in FIG. 5. The bracket serves as a housing to protect the connector which connects a fluid supply tube to a fluid delivery tube.

Figure 6:
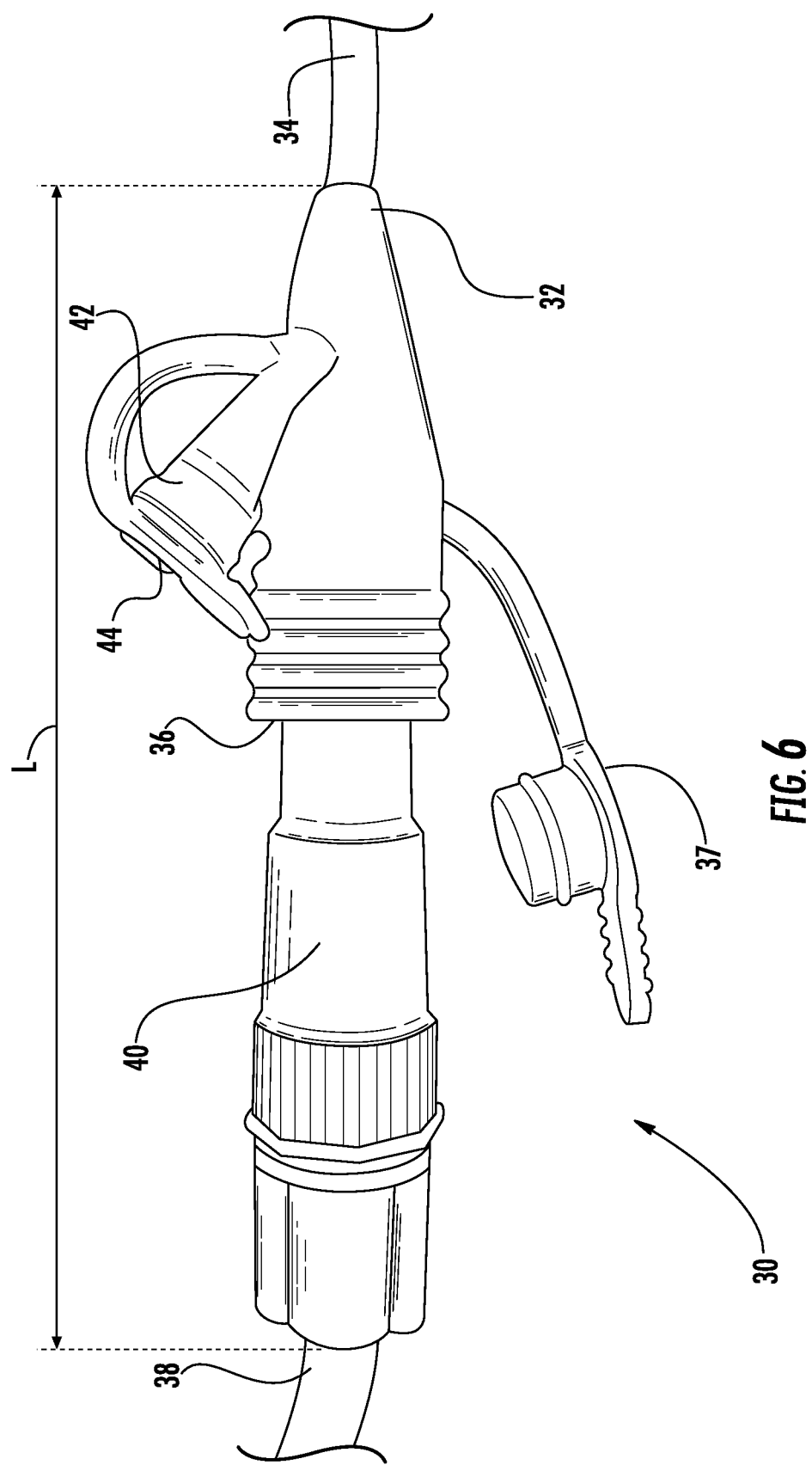
FIG. 6 shows a top plan view of an exemplary feeding tube Y-port connector that can be supported by the bracket shown in FIGS. 1-4.

FIG. 6 illustrates a representative Y-port connector 30, which has an outlet end 32 connected to the gastric feeding tube 34 and an inlet end 36 configured to receive a stepped connector 40 joined to a delivery tube 38 extending from a source of nutritional product (not shown). A medication port 42 includes a first plug 44 to close the medication port 42 when not in use. A second plug 37 closes the inlet end of the Y-port connector 30 when the port is not being used for feeding.

The bracket 10 has side walls 14, 16, rear or bottom wall 22, and end walls 18, 20, that surround and define a central pocket 12. Front wall 27 is positioned above the central pocket 12. A first port plug receiving portion comprises a space 13 adjacent to the central pocket 12 near the side wall 14. A second port plug receiving portion comprises a cavity or space 33 adjacent to the central pocket 12 formed in a portion of the side wall 16. The central pocket 12, cavity or space 13 and space 33 together form a multi-section pocket. In embodiments, the disclosed bracket 10 is roughly rectangular, with rounded corners to avoid patient discomfort and reduce snagging on bedding or clothing. The concept is not limited to a rectangular exterior shape, with the functional dimensions of the central pocket 12, cavity or space 13 and space 33 being defined by the inside surfaces of the side walls 14, 16, end walls 18, 20 and bottom wall 22.

The length L of the central pocket 12 corresponds to the length dimension L of the distance between the outlet end 32 of the Y-port connector 30 and the enlarged outer end of the stepped connector 40 joined to the source of nutritional product. This dimension L may vary depending upon the manufacturer of the Y-port connector 30 and stepped connector 40. Bracket 10 end wall 18 defines a slot 19 formed by U-shaped wall 29 between shoulders 17a and 17b. The slot 19 is dimensioned to allow the tube 38 to be placed in the slot 19 without restriction, while retaining the stepped connector 40 inside the pocket 12. In some embodiments, the slot 19 is configured to provide an interference fit with the tube 38 without obstructing flow through the tube 38.

Bracket end wall 20 defines a slot 21 formed by U-shaped wall 31 between shoulders 23a and 23b. The slot 21 is dimensioned to permit tube 34 to be inserted in the slot 21 without restriction, while retaining the outlet end 32 of the Y-port connector inside the pocket 12. In embodiments, the slot 21 is configured to provide an interference fit with the tube 34 without obstructing flow through the tube 34. The disclosed bracket configuration supports the assembled Y-port connector 30 and stepped connector 40 and keeps the stepped connector 40 in position during feeding. The substantially rigid structure of the bracket 10 maintains alignment of the couplings and tubes to reduce unintended restrictions during feeding, resulting in fewer alarms.

In embodiments, the connector 40 is a stepped connector, but a non-stepped connector, such as a tapered connector can be used in place of the stepped connector. As indicated above, in some embodiments, the interference fit that holds the tubes in the bracket is between the slot walls of the bracket and the outer walls of the tubes. In other embodiments, the interference fit is between the bracket wall portion inside the bracket 10, near the slot 21 and the outlet end of the Y-port connector, and between the bracket wall portion inside the bracket 10 near slot 19 and the inlet end of the stepped connector 40. In still other embodiments, combinations of these two types of interference fit can be employed.

In embodiments, instead of using an interference fit, the medical tubes and connectors are held in place in slots 19 and 21 by other suitable support mechanisms.

As best seen in FIG. 5, the central pocket 12 is adjacent to the space 13, i.e. the first port plug receiving portion, to accommodate the plug 37 associated with the inlet end 32 of the Y-port connector 30. The space 13 is defined by the inner surface 50 of the side wall 16, and angled first plug receiving walls 52 and 54. Space 13 is configured to accommodate the first plug 37 when the plug 37 is in an open position. In embodiments, the space 13 is configured with a size and shape suitable to accommodate the lift tab 56 of the first plug 37, the nipple 51, and the tether 60 that connects the plug 37 to the Y-port connector 30. In embodiments, the depth of the space from the central pocket 12 to the inner surface 50 of the side wall 16 is about ⅛ inch larger than the depth of the nipple 58. In embodiments, space 13 is continuous with a portion of the central pocket 12. FIG. 5 shows points providing an interference fit in one embodiment. Stepped connector 40 contacts the internal wall of the bracket 10 at 45 and 46. Y-port connector 30 contacts the internal walls of the bracket 10 at 47 and 48. In embodiments, the outer walls of tubes 38 and 34 contact the walls of slots 19 and 21, respectively.

In the embodiment shown in FIGS. 1-5, the central pocket 12 is also adjacent to the space 33, i.e. the second port plug receiving portion, to accommodate the plug 44 associated with the medication port 42. The inner side 62 of side wall 14 includes a protruding ledge 11 arranged to contact the medication port plug 44 to maintain this port in a closed condition while the assembled Y-port connector 30 and stepped connector 40 are in the bracket central pocket 12. In embodiments, the space 33 is continuous with a portion of the central pocket 12.

Figure 7:
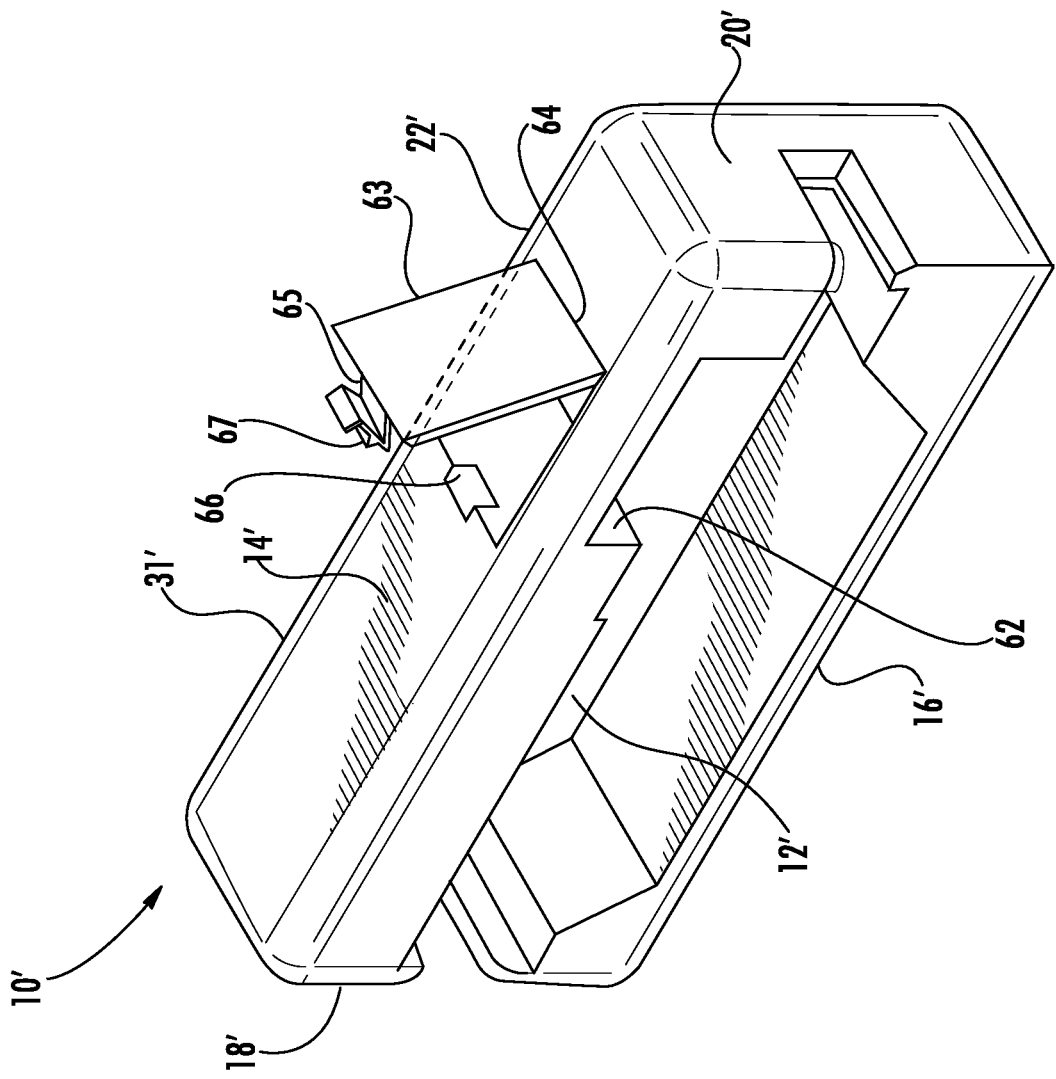
FIG. 7 shows a perspective view of a second embodiment that includes a door that can be opened for access to a second inlet port.

In an alternative embodiment of the bracket 10' shown in FIG. 7, which includes side walls 14', 16', rear or bottom wall 22', end walls 18', 20' and central pocket 12', the bracket 10' may be provided with a side door 63 mounted on side wall 14'. The side door 63 is positioned to permit opening of the medication port while the tubes are in the bracket 10'. In the embodiment shown, the door 63 has a hinge 64 and a closure tab 65. The closure tab 65 has a V-shaped cross section and includes an extension portion 67 that engages with opening 66 in side wall 14' and interior wall 62 to latch the side door 63 in a closed position. In FIG. 7, the door is shown in an open position.

Figure 8:
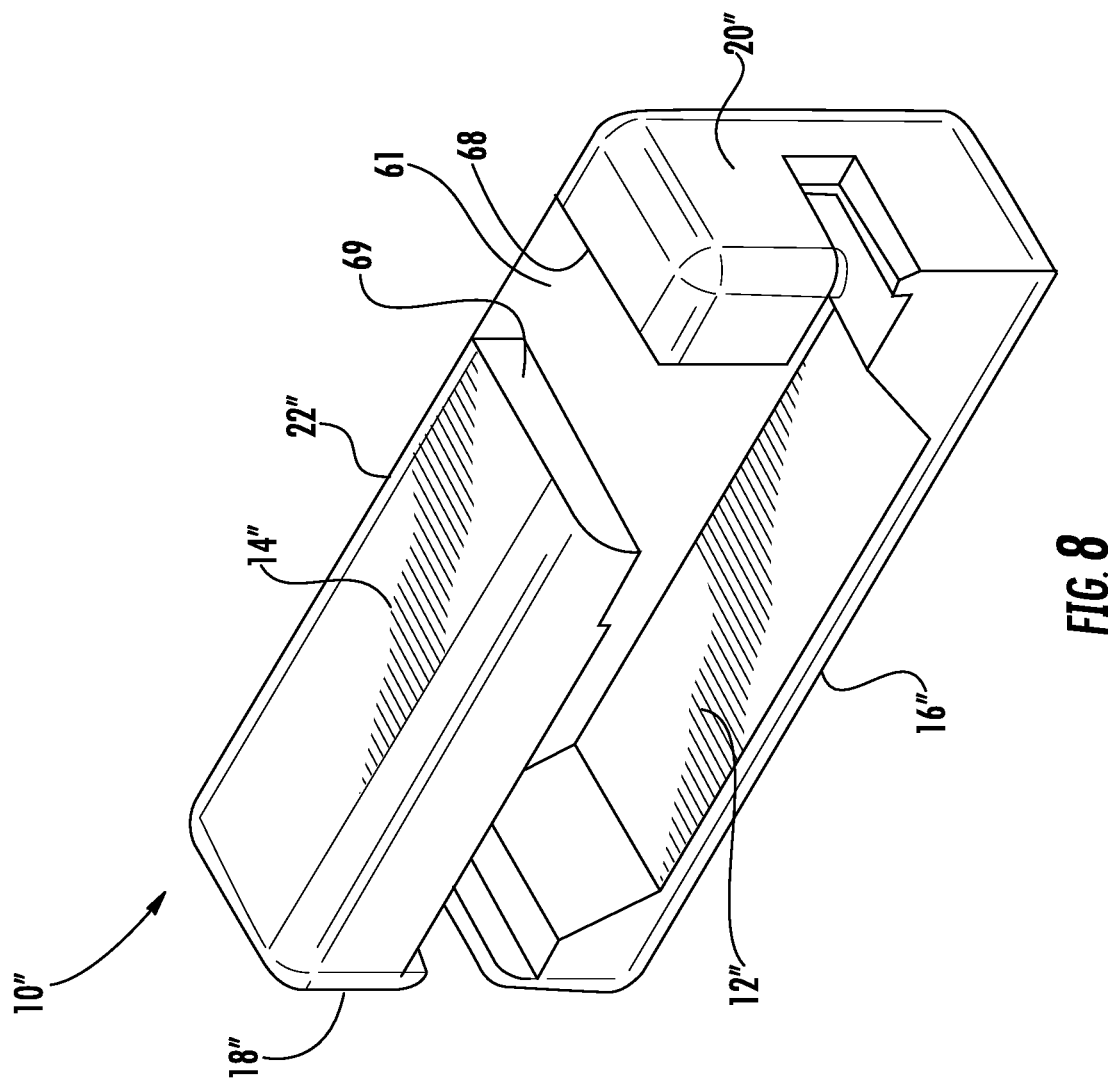
FIG. 8 shows a perspective view of a third embodiment that includes an opening for access to a second inlet port.

In an alternative embodiment shown in FIG. 8, the bracket 10" includes side walls 14", 16", rear or bottom wall 22", and end walls 18" and 20". The bracket 10" has an opening 61 in wall 14" defined by opposed walls 68 and 69, and the inner surface of rear or bottom wall 22". The opening 61 is configured to permit opening of the medication port, and connection of the medication port to a medication supply source.

Figure 9:
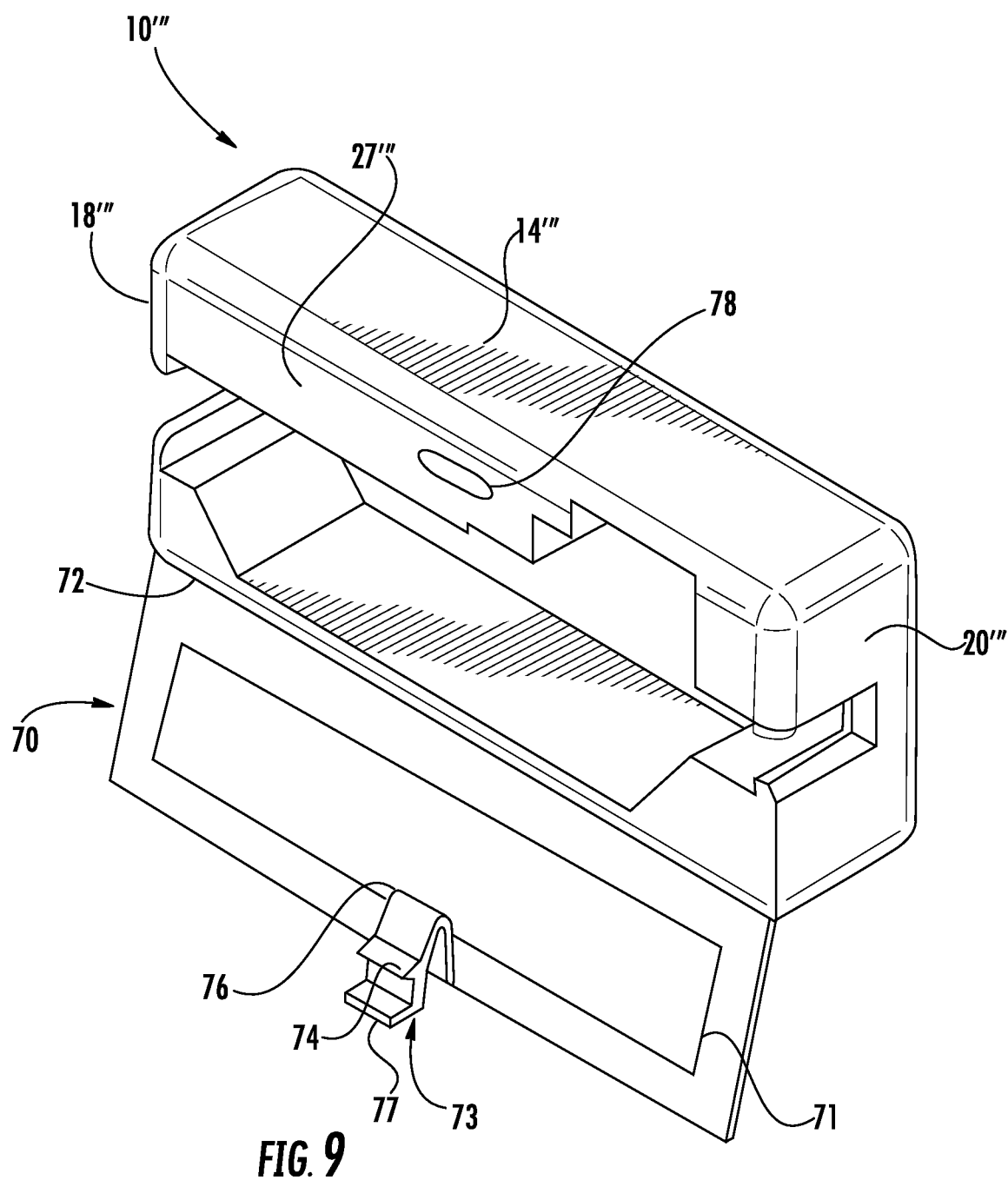
FIG. 9 is a perspective view of a fourth embodiment that includes a front wall with a viewing window.

In a further alternative embodiment shown in FIG. 9, the bracket 10''' may be provided with a front door or cover 70 to enclose the central pocket 12''', space 13''' and/or space 33'''. In the embodiment shown in the Figure, the bracket 10''' includes side walls 14''', 16''', rear or bottom wall 22''', and end walls 18''' and 20'''. The front door 70 is mounted by hinge 72. The front door includes a substantially clear viewing window 71 configured to allow a viewer to confirm that the tubes are properly connected to a Y-port connector when the connector is mounted in the bracket. FIG. 9 shows the door in an open position. The front door 70 can be latched in a closed position using latch 73, which includes a V-shaped resilient portion 76, an extension portion 74 and a finger engagement portion 77. The resilient portion 76 and extension portion 74 are received in an aperture 78 formed in front wall 27'''. In other embodiments, the cover may be a separate part configured to snap onto the bracket 10 rather than being connected to the bracket by a hinge. In embodiments, the door can be a sliding door rather than a pivoting door.

Figure 10:
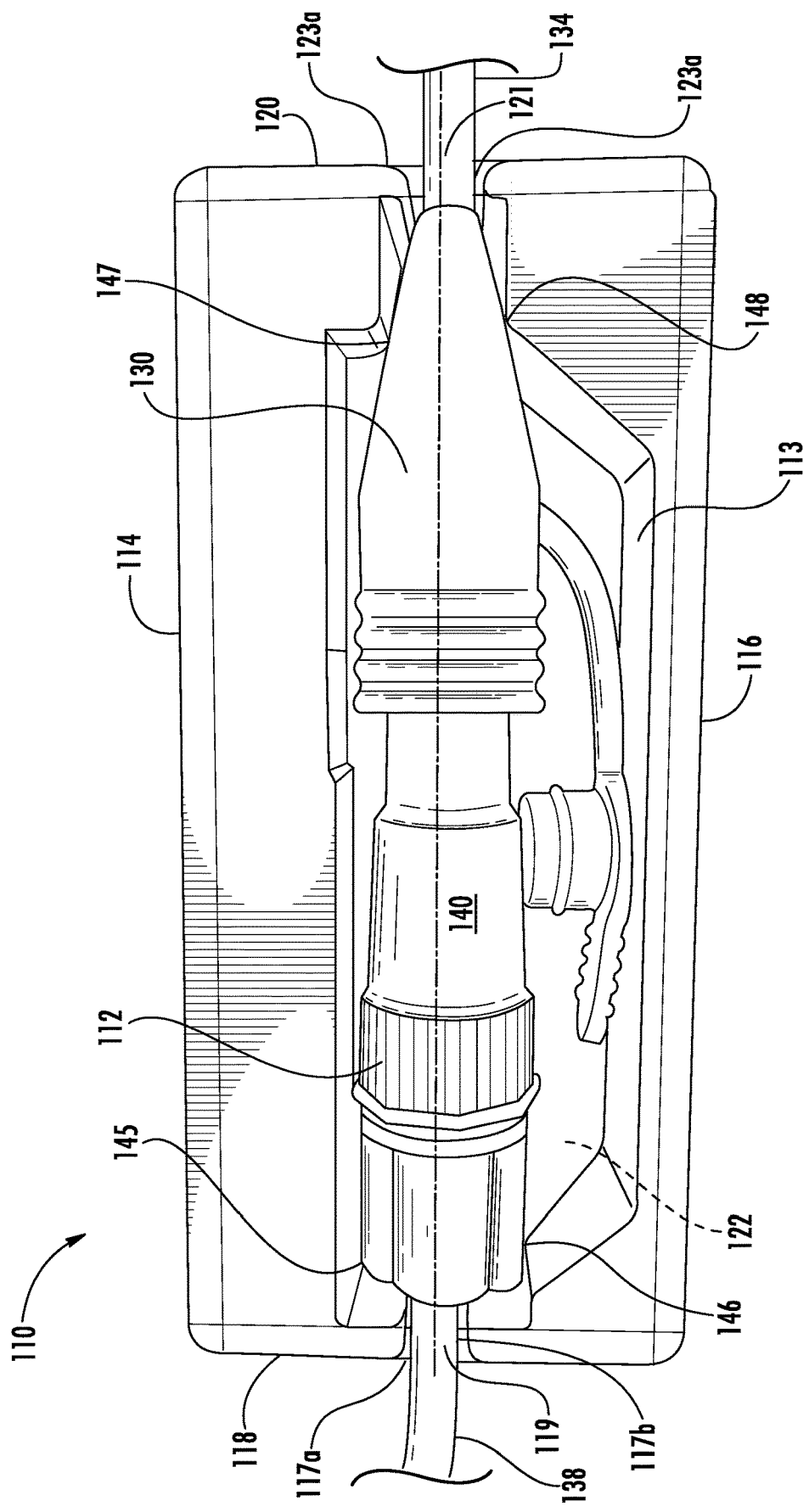
FIG. 10 is a top plan view of a fifth embodiment of a bracket that supports a fluid delivery tube that has only one fluid supply port.

FIG. 10 shows an embodiment of a bracket 110 that includes a central pocket 112 and a space 113 but does not include a space for second plug. This embodiment is intended for use with a fluid delivery line that includes only one inlet port. Similar to the embodiment shown in FIGS. 1-5, the bracket 110 shown in FIG. 10 is a single piece substantially rigid part that defines a central pocket 112 and an adjacent space 113 that are configured to receive and retain an assembly of a port connector, a fluid supply tube and an associated fluid delivery tube.

The bracket 110 comprises a housing that has side walls 114, 116, rear wall 122, and end walls 118, 120, that surround and define a central pocket 112 and an adjacent space 113. In embodiments, the disclosed bracket 110 is roughly rectangular, with rounded corners to avoid patient discomfort and reduce snagging on bedding or clothing. The concept is not limited to a rectangular exterior shape, with the functional dimensions of the pocket 112 and space 113 being defined by the inside surfaces of the side walls 114, 116, end walls 118, 120 and bottom wall 122.

The length L of the central pocket 112 corresponds to the length dimension L of the distance between the outlet end 132 of a port connector 130 and the enlarged outer end of the stepped connector 140 joined to the source of nutritional product. This dimension L may vary depending upon the manufacturer of the port connector 130 and stepped connector 140. Bracket 110 end wall 118 defines a slot 119 between shoulders 117a and 117b. The slot 119 is dimensioned to allow the tube 1384 to be placed in the slot 119 without restriction, while retaining the outlet end 132 of the port connector inside the pocket 12. In embodiments, the slot is configured to provide an interference fit with the tube 138 without obstructing flow through the gastric feeding tube 138. Bracket end wall 120 defines a slot 121 between shoulders 123a and 123b. The slot 121 is dimensioned to permit tube 134 to be inserted in the slot 121 without restriction, while retaining the stepped connector 140 inside the pocket 112. The disclosed bracket configuration supports the assembled connector 130 and stepped connector 140 and keeps the stepped connector 140 in position during feeding. The substantially rigid structure of the bracket 110 maintains alignment of the couplings and tubes to reduce unintended restrictions during feeding, resulting in fewer alarms.

FIG. 10 shows locations providing an interference fit in one embodiment. Stepped connector 140 contacts the bracket at 145 and 146. Y-port connector 30 contacts the bracket at 147 and 148. In embodiments, the outer walls of tubes 138 and 134 contact the walls of slots 119 and 121, respectively.

Figure 11:
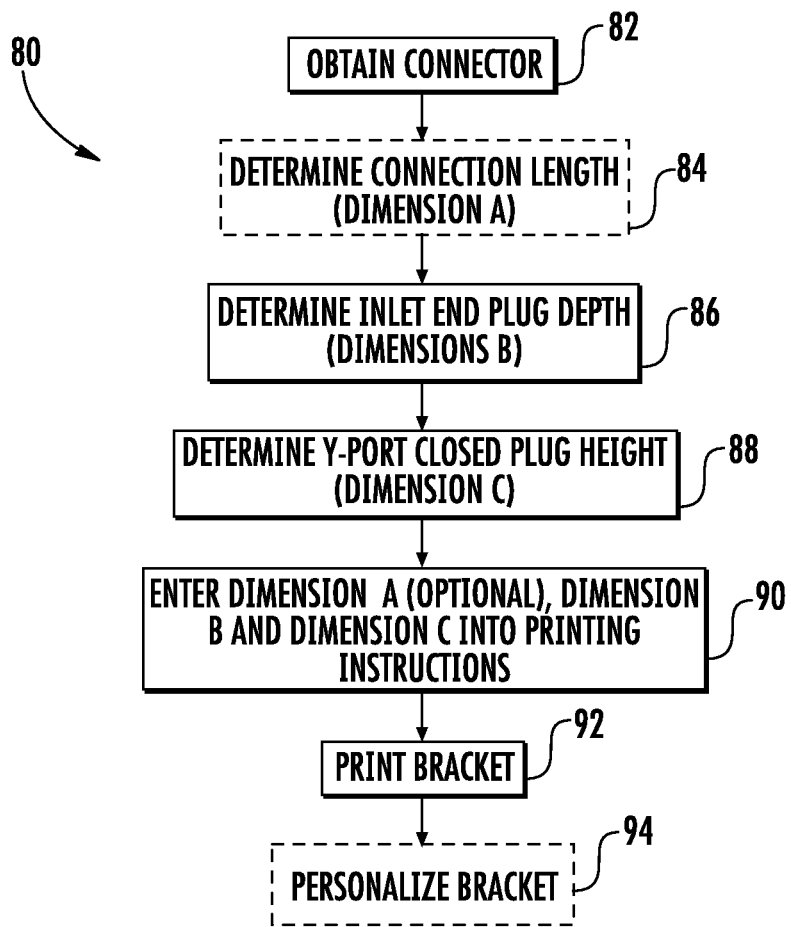
FIG. 11 is a flow chart showing an embodiment of a method of making the brackets shown above.

In some cases, the bracket is 3D printed. An exemplary printing method is shown in FIG. 11 and is designated as 80. First, a connector to be protected by a bracket is obtained at 82. Optionally, the connector length (Dimension "A") is determined at 84. For example, the length can be determined by imaging the connector or by receiving data enter by a user. In some embodiments, a standard bracket length is used and measurements are not required. The end plug depth (Dimension "B") is determined at 86. The Y-port closed plug height (Dimension "C") is determined at 88. Dimensions "A" (optional), "B" and "C" are entered into printing instructions at 90, and the bracket is 3D printed at 92. The bracket optionally is personalized at 94 by decorating, engraving, etc. This method allows for efficient custom printing of brackets for specific users and for port connectors of different sizes.

In embodiments, the 3D printing method is adapted for 3D printing of brackets for connectors that have only one inlet port.

In embodiments, the disclosed bracket 10 or 110 is intentionally simple and includes no moving parts that can be separated or lost. The disclosed bracket may be manufactured by a variety of well-known methods, including 3D printing (as indicated above), injection molding, machining or the like. The bracket 10 or 110 may be made from a variety of materials that provide the desired properties of durability, safety and structural integrity. The bracket 10 or 110 may be rigid or substantially rigid, meaning materials such as silicone or rubber may be used. Metals or other rigid materials may also be used. The bracket may be color coded or may be manufactured from materials that glow in the dark, which would facilitate finding the bracket during night feedings. The bracket could be transparent as well. The bracket 10 or 110 may be decorated or engraved for specific patients. The bracket 10 or 110 is not restricted to the rectangular outside shape that is disclosed and could be any shape including rounded, circular, square, triangular, diamond shaped, or any shape that may be aesthetically pleasing.

In embodiments, the bracket comprises a thermoplastic or thermoset polymeric material. Non-limiting examples of suitable materials include polyethylenes, polypropylenes, copolymers and/or terpolymers containing polyethylenes, copolymers and/or terpolymers containing polypropylenes, polyesters, including biodegradable thermoplastic polyesters including but not limited to polylactic acid (PLA), and butadienes including but not limited to acrylonitrile butadiene styrene (ABS).

In embodiments, the bracket 10 or 110 may be modular in construction, with parts that snap together to define a pocket 12 that can be re-configured for alternative Y-ports and food delivery connectors. The bracket 10 or 110 may be provided with a clip or other attachment means to secure the bracket to clothing or person of the patient receiving nutrition. The bracket 10 or 110 may be configured to protect Nasal Gastric (NG) Tubes, Gastric (G) Tube, Intravenous (IV) lines, Tracheostomy Tubes, and other Medical Ports and Lines. The bracket 10 or 110 could be made to cap off just the main port (such as 36), leaving access to the medical port.

It will be appreciated that features disclosed above and other features and functions, or alternatives thereof, may be desirably combined into many other different systems or applications. Furthermore, currently unforeseen or unanticipated alternatives, modifications, variations or improvements therein may be subsequently made by those skilled in the art which are also intended to be encompassed by the following claims.

What is claimed is:

1. A fluid delivery tube bracket, comprising:
   a central pocket formed by a rear wall, substantially parallel first and second end walls disposed at opposite terminal ends of the bracket, and first and second side walls,
       the first end wall having a first slot defined by opposite first and second shoulders and being configured to receive a first medical tube, the first slot extending to a front wall of the bracket, providing a first opening in the front wall,
       the second end wall having a second slot defined by opposite third and fourth shoulders and being configured to receive a second medical tube, the second slot extending to the front wall of the bracket, providing a second opening in the front wall,
       the first side wall including a first port plug receiving portion configured to receive a first port plug when in an open position, and
       the second side wall including a second port plug receiving portion comprising a cavity formed in a portion of the second side wall configured to support a second port plug when in a closed position, the cavity being defined by a surface configured to support a plug, the surface having a length that is smaller than the length of the second side wall.

2. The bracket of claim 1, wherein the front wall of the bracket has an open portion configured to permit viewing of the central pocket.

3. The bracket of claim 1, wherein the front wall comprises a viewing window.

4. The bracket of claim 1, wherein the bracket is substantially rigid.

5. The bracket of claim 1, wherein the bracket has a one-piece construction.

6. The bracket of claim 1, wherein the first and second slots are configured to support first and second medical fluid delivery tubes, respectively, with an interference fit.

7. The bracket of claim 1, wherein the bracket is formed from a thermoplastic or thermoset polymeric material.

8. The bracket of claim 1, wherein the second side wall has a door formed thereon configured to permit connection to a second fluid source when the second port plug is in an open position.

9. The bracket of claim 1, wherein the second side wall has an opening formed therein configured to receive a third medical tube.

10. A medical tube system comprising:
    a Y-port connector having an outlet end connected to a fluid delivery tube and an inlet end connected to a fluid supply tube, the Y-port connector including a first port at the inlet end configured to receive a first plug, and a second port configured to receive a second plug, and
    a medical fluid delivery tube bracket comprising a central pocket formed by a rear wall, substantially parallel first and second end walls formed at opposite terminal ends of the bracket, and first and second side walls,
        the first end wall having a first slot defined by opposite first and second shoulders and being configured to receive the fluid supply tube,
        the second end wall having a second slot defined by opposite third and fourth shoulders and being configured to receive the medical fluid delivery tube,
        the first side wall including a first port plug receiving portion configured to receive a first port plug when in an open position, and the second side wall including a second port plug receiving portion comprising a cavity formed in a portion of the second side wall configured to support the second port plug when in a closed position, the cavity being defined by a surface configured to support a plug, the surface having a length that is smaller than the length of the second side wall.

11. The system of claim 10, wherein the bracket has an open front configured to permit viewing of the central pocket.

12. The system of claim 10, wherein the bracket has a front wall comprising a viewing window.

13. The system of claim 10, wherein the bracket is substantially rigid.

14. The system of claim 10, wherein the bracket has a one-piece construction.

15. The system of claim 10, wherein the bracket is formed from a thermoplastic or thermoset polymeric material.

16. The system of claim 10, wherein the second side wall has a door formed thereon configured to permit connection to a second fluid source when the second port plug is in an open position.

17. The system of claim 10, wherein the second side wall has an opening formed therein configured to receive a third medical tube.

18. A bracket for a fluid delivery tube, the bracket comprising:
    a central pocket formed by a rear wall, first and second end walls, and first and second side walls,
        the first end wall having a first slot defined by opposite first and second shoulders and being configured to receive a first medical tube, the first slot extending to a front wall of the bracket, providing a first opening in the front wall,
        the second end wall having a second slot defined by opposite third and fourth shoulders and being configured to receive a second medical tube, the second slot extending to the front wall of the bracket, providing a second opening in the front wall,
        the first side wall having a first port plug receiving portion configured to receive a port plug when in an open position,
        the second side wall including a second port plug receiving portion comprising a cavity formed in a portion of the second side wall configured to support a second port plug when in a closed position, the cavity being defined by a surface configured to support a plug, the surface having a length that is smaller than the length of the second side wall, wherein the front wall comprises a front cover with a substantially clear viewing window to permit viewing inside the central pocket.

* * * * *